United States Patent [19]

Lynch et al.

[11] Patent Number: 4,830,757
[45] Date of Patent: May 16, 1989

[54] TELEMETRY SYSTEM FOR WATER AND ENERGY MONITORING

[75] Inventors: John T. Lynch; Hadley M. Hurford, Jr., both of Mayfield Heights, Ohio

[73] Assignee: The Mogul Corporation, Solon, Ohio

[21] Appl. No.: 34,020

[22] Filed: Oct. 13, 1987

Related U.S. Application Data

[63] Continuation of Ser. No. 762,858, Aug. 6, 1985, abandoned.

[51] Int. Cl.⁴ .............................................. C02F 1/66
[52] U.S. Cl. .................... 210/742; 210/743; 210/744; 210/746; 210/85; 210/86; 210/96.1; 210/104; 210/143; 210/149; 340/540; 364/500
[58] Field of Search ............... 210/739, 742, 743, 746, 210/85, 96.1, 138–143, 149, 86, 104, 744; 340/540, 679; 364/500, 510

[56] References Cited

U.S. PATENT DOCUMENTS

| | | | |
|---|---|---|---|
| 4,246,101 | 1/1981 | Selby, III | 210/96.1 |
| 4,536,845 | 8/1985 | DeVale et al. | 210/143 |
| 4,563,272 | 1/1986 | Yoshida et al. | 210/93 |
| 4,631,530 | 12/1986 | Gasper | 210/739 |
| 4,639,718 | 1/1987 | Gasper | 210/85 |
| 4,648,043 | 3/1987 | O'Leary | 364/510 |
| 4,659,459 | 4/1987 | O'Leary et al. | 210/87 |

OTHER PUBLICATIONS

Satake et al., "Series of Digital Control System for Water & Sewage Equipment", *Fugi Electric Review*, 1981, pp. 86–92.
Ito et al., "Micro-Controller System for Water and Sewage Works," *Fugi Electric Review*, 1978, vol. 24, No. 1.
Kashiwagi et al., "Computer Control System for Water & Wastewater Treatment Plants," *Hitachi Review*, 1978, pp. 144–152.

*Primary Examiner*—Peter Hruskoci
*Attorney, Agent, or Firm*—Pearne, Gordon, McCoy & Granger

[57] ABSTRACT

A water quality monitor computer (10) repeatedly accesses transducers (12) which monitor physical properties of a water system, such as total dissolved solids, pH, and the like. The water quality monitor computer determines from the monitored water conditions when bleeding or the addition of water treatment chemicals is required. An energy and water management computer (20) periodically accesses the water quality computer and operates valves and pumps (22) to bleed the system or add chemicals, as is appropriate. The management computer further monitors the quantity of chemical supplies on hand with chemical inventory transducers (24), the amount of electrical energy consumed with kilowatt transducer (28) and the like. The energy and water management computer controls energy usage and stores energy and chemical consumption data in a memory (40). A polling station (B) selectively polls one or more of the remote stations to change the energy or water management programs or to receive data and water system physical property data therefrom. One of the polling stations includes a central computer (250) which polls each remote station daily. The central computer causes a printer (254) to generate daily reports indicating abnormal conditions at each remote station and to generate shipping orders and invoices for replacement chemicals as replacement becomes necessary. The central polling computer also generates a monthly report of energy and chemical consumption, water treatment system physical property data, energy savings, and the like.

17 Claims, 7 Drawing Sheets

TELEMETRY SYSTEM FOR WATER AND ENERGY MONITORING

This is a continuation, of application Ser. No. 762,858, filed 08/06/85, now abandoned.

BACKGROUND OF THE INVENTION

The present invention relates to the art of automatic control systems. It finds particular application in conjunction with the control of building maintenance functions, particularly coordinated and combined control of water treatment and energy usage facilities and will be described with reference thereto. It is to be appreciated, however, that the invention also finds other applications including automatic maintenance of boiler, cooling tower water chemistry, control of water treatment chemistry, control of chemical processing chemistry, control of chemical manufacturing, and the like.

Heretofore, various computer based controllers have been developed for monitoring and managing the electrical energy usage of office buildings and the like. However, the treatment of water in the cooling tower was left substantially to human control. Inept and unskilled human management of the cooling tower or boiler water has frequently resulted in unnecessary expense and a loss of efficiency.

Cooling tower water and boiler water need periodic chemical adjustment to provide efficient cooling and heat transfer. For example, biocides are added to kill algae and other organisms that breed in the warm water. As the warm water evaporates, the concentration of calcium, magnesium, and other water dissolved chemicals which tend to coat and insulate heat transfer apparatus increases reducing heat transfer efficiency. The deposition of calcium and magnesium is fought by the periodic bleeding and replacement of the high dissolved chemical concentration water and by the addition of deposition inhibiting chemicals. Other chemicals are commonly added to inhibit corrosion, adjust pH, complex suspended particulates, and the like.

Equipment has been developed for monitoring these and other chemical properties. However, the addition of appropriate amounts of chemicals is commonly left to human operators and human error. In many instances, the human operators are general building maintenance personnel that are untrained in water treatment chemistry and procedures. Money was wasted by adding too much of some water treatment chemicals, while cooling or heating efficiency were cut by adding too little of others.

To reduce the required human maintenance and accompanying human error, others have suggested apparatus for the automatic addition of chemicals and the automatic bleeding of a percentage of the cooling water. However, this equipment too was subject to failure. When chemical additive pumps or valves stuck in a feed state, large amounts of treatment chemicals were wastefully added until the supply drum went dry. Thereafter, the treatment chemical was unavailable for addition until the next scheduled supply drum replacement. The addition of unnecessary chemicals is financially wasteful, not only in the cost of excess chemicals but also in the loss of heat transfer efficiency. When the treatment chemical addition pumps or valves failed in a flow blocking state, the supply drums ran dry, or bleed valves stuck closed, heat transfer efficiency was reduced. When bleed valves are stuck open, excessive water removal could irreparably damage the entire system.

The present invention contemplates a new and improved control system which automatically monitors water quality, such as conductivity, pH, temperature, chemical quantity on hand, impurities, and the like. Appropriate provision is made for adjusting the chemical composition of the water to maintain the water quality within selected ranges and to guard against system malfunction.

SUMMARY OF THE INVENTION

In accordance with one aspect of the present invention, water treatment and energy usage are telemetrically monitored. At each of a plurality of remote locations, a physical property indicative of water quality is monitored. Concurrently, energy usage at the remote location is monitored. Periodically, e.g. once an hour the monitored physical property level and the amount of used energy are stored. The physical property levels and energy usage stored at the remote locations are polled periodically, e.g. once a day, from a polling location.

In accordance with a more specific application of the present invention, the monitored physical property is compared with a preselected physical property range or set points to determine whether an adjustment to the water is indicated. Adjustments to the chemical properties of the water are automatically made in response to the monitored physical property level being outside the preselected physical property range. The chemical property adjustment may include bleeding water from the system and replacing it with fresh water, adding treatment chemicals, and the like.

In accordance with another aspect of the present invention, a method of maintaining water treatment quality is provided. At each of a plurality of remote locations, at least one physical property indicative of water quality is monitored. Each monitored physical property is compared with a corresponding physical property set point range. In response to one of the monitored physical properties falling outside the corresponding range, a corresponding chemical is added to adjust the water quality. The amount of each chemical on hand at the remote location is monitored and stored. From a polling location, the quantity of each stored chemical in each of the plurality of remote locations is periodically polled and compared with corresponding chemical quantity specifications. In response to the polled chemical quantity being outside the chemical quantity specification, shipment of additional chemical to the appropriate remote location is automatically invoiced.

In accordance with yet another aspect of the present invention, a telemetry system is provided for monitoring water treatment chemical energy usage. The system includes a plurality of remote monitoring stations and at least one polling station. Each remote monitoring station includes a water monitor for monitoring a physical property indicative of water quality and means for comparing the monitored physical property level with a preselected range or set point to determine whether or not an adjustment to the water is indicated. Each remote station also includes an energy monitoring means for monitoring energy usage and a storage means for storing the monitoring physical property level and the monitored energy usage. At the polling station, a computer periodically polls and stores the physical property levels and the energy usage stored at each of the plurality of remote locations. Optionally, the polling computer may generate various reports of chemical and energy usage, excessive or insufficient chemical usage, other malfunctions and emergencies, invoices for shipping additional treatment chemicals, and the like.

One advantage of the present invention is that it reduces cost and improves efficiency.

Another advantage of the present invention is that it optimizes water treatment chemical usage and reduces the discharge of cooling tower water into public water disposal systems.

Yet another advantage of the present invention is that it monitors for system malfunctions, enables skilled water treatment engineers to maintain a plurality of remote treatment systems from a common location, and maintains a history of chemical usage while reducing man power requirements.

Still further advantages of the present invention will become apparent to those of ordinary skill in the art upon reading and understanding the following detailed description of the preferred embodiment.

BRIEF DESCRIPTION OF THE DRAWINGS

The present invention may take form in various steps and arrangements of steps or in various parts and arrangements of parts. The drawings are only for purposes of illustrating a preferred method and apparatus for carrying out the present invention and should not be construed as limiting the invention.

DETAILED DESCRIPTION OF THE PREFERRED EMBODIMENT

Figure 1A:
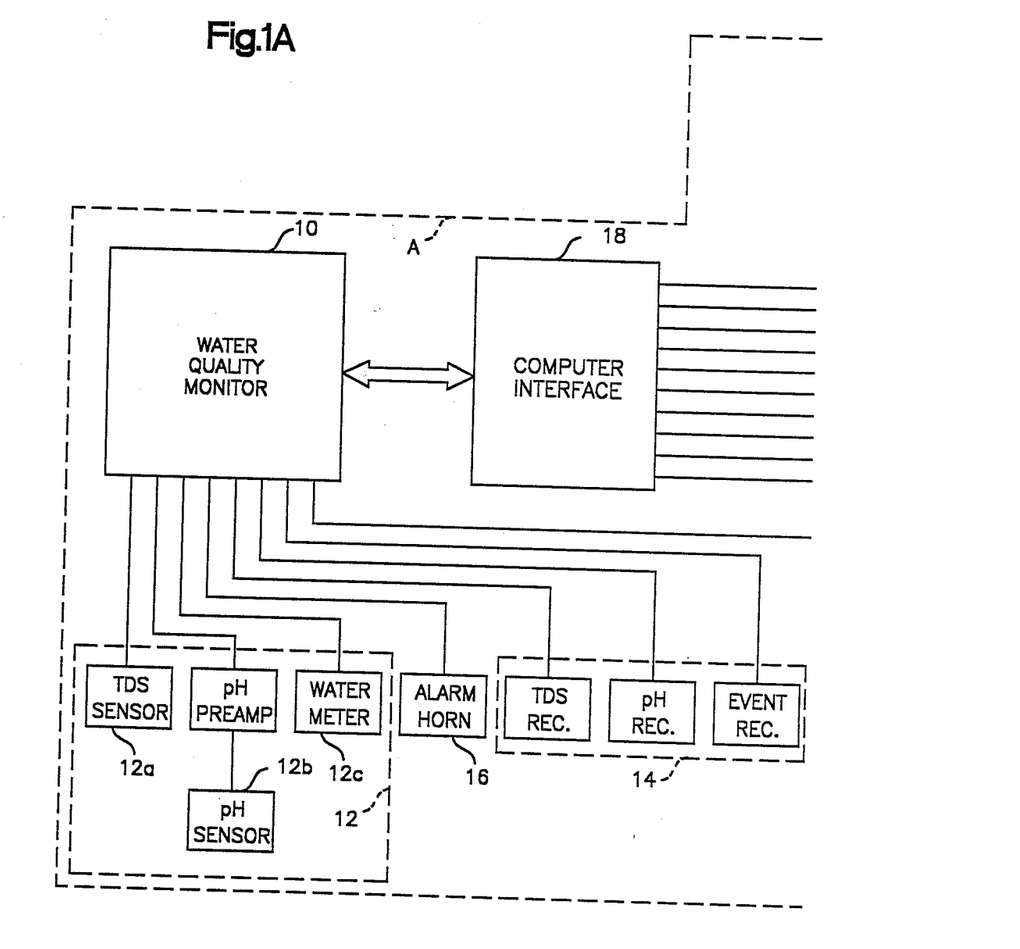
FIGS. 1A and 1B taken together constitute a block diagram of a telemetry system in accordance with the present invention.
Figure 1B:
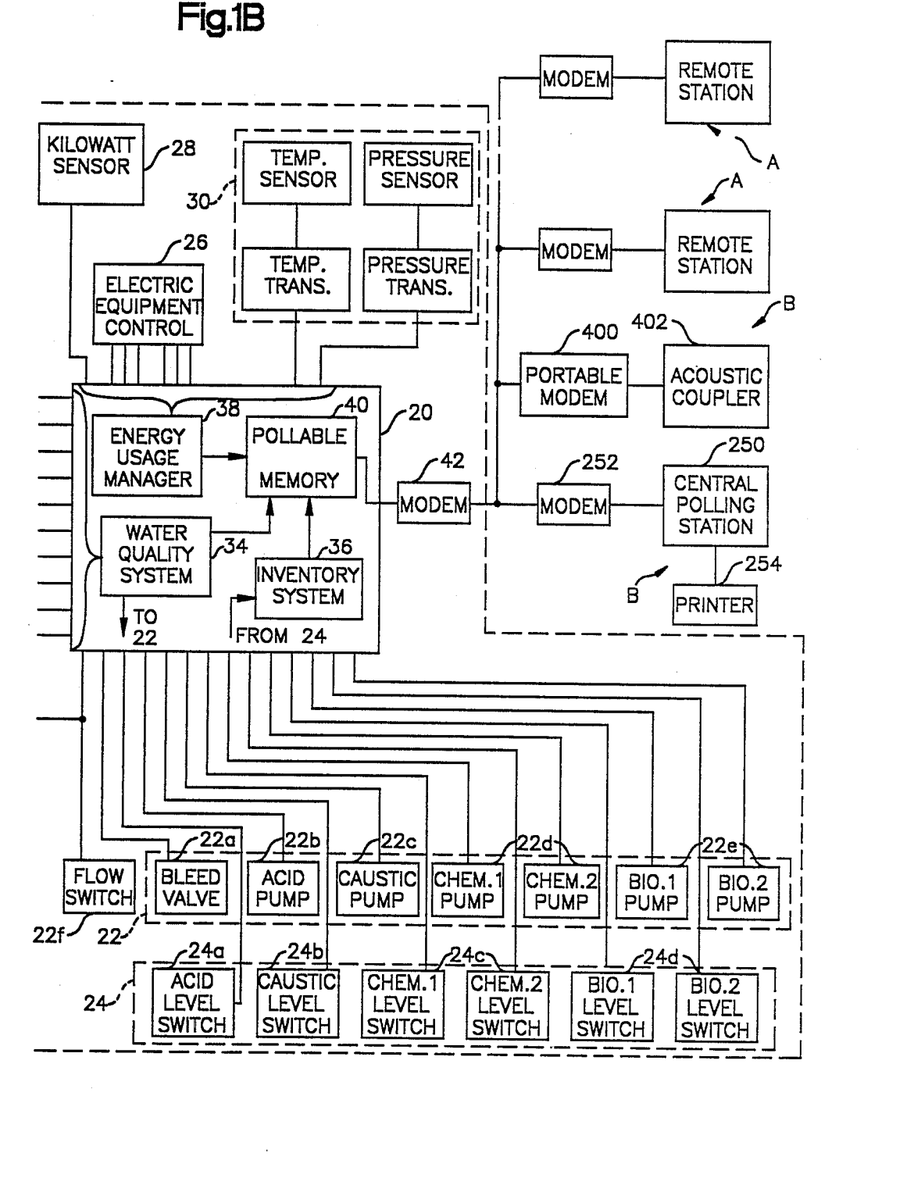

With reference to FIGS. 1A and 1B, a plurality of remote stations A are interconnected by telephone lines with one or more central polling stations B. Each remote station monitors a cooling tower, boiler, scrubber, dust collector, or other water system for physical properties which are indicative of water quality. These physical properties include conductivity, pH, temperature, levels of various chemicals within the water, impurities, and the like. In response to the monitored physical property levels, water is bled off or chemicals are added, as may be appropriate. Further, each remote station monitors and manages electrical and other energy usage. The monitored physical property levels of the water, bleed times, amounts and periodicity of the addition of chemicals, the amount of chemicals on hand, energy usage, and the like are monitored and stored at each remote station.

The stored water treatment, chemical, and energy data are periodically polled, e. g. every 24 hours, by the central polling station B. The polling station generates various reports including periodic reports of chemical and energy usage, emergency reports indicating system malfunctions, and the like. The central polling computer further generates invoices to ship replacement chemicals as a supply at each remote station becomes low. In this manner, each remote station is remotely checked for proper operation and for proper inventories of chemical supplies.

Moreover, each remote station A can be selectively accessed from any telephone and selected portions of the stored data retrieved. This enables salesmen, engineers or other personnel to monitor chemical inventories, to monitor system malfunctions, reprogram a remote station with appropriate corrections, and the like.

With continuing reference to FIGS. 1A and 1B, each of the remote stations is of similar construction. Accordingly, an exemplary remote station is illustrated in detail and it is to be understood that the description applies by analogy to the other remote stations. Each remote station includes a water quality monitor computer 10 which monitors one or more physical properties of water in a cooling tower or other water system. A plurality of physical property sensors 12 sense the levels of the selected physical properties of the water to provide an input for the water quality monitor computer 10. A conductivity sensor 12a measures for total dissolved solids, a pH sensor 12b measures pH, and a water meter 12c measures the receipt of fresh water. The physical properties are indicative of water quality and may include conductivity, pH, temperature, chemical concentration, the level of impurities, and the like. A plurality of recorders 14 record the monitored physical properties to provide a record and display thereof. An alarm 16, such as a horn, provides an audio or visual warning of a detected malfunction, such as an inability of the system to hold a monitored physical property in the preselected range.

The water quality monitor computer 10 compares each monitored physical property level with a corresponding preselected range to determine whether an adjustment to the monitored water is called for. If an adjustment is indicated, the water quality monitor computer provides the appropriate output signals to cause appropriate amounts of appropriate chemicals to be added. The monitored physical properties and the water management control signals for bleeding water or adding selected chemicals are conveyed by a computer interface 18 to an energy and water management computer 20. Optionally, the water quality monitor computer and the management computer may be combined in a common computer and the interface eliminated.

The management computer 20 is interconnected with a plurality of water quality control valves, pumps, or other means 22. The water quality is controlled by a bleed valve 22a for bleeding water from the system, an acid pump 22b and a caustic pump 22c for adjusting the pH, water treatment chemical pumps 22d, biocide pumps 22e for adding chemicals to kill organisms in the water, and the like. A flow switch 22f monitors whether fresh water is being added.

An electrical energy control system 26 selectively actuates and de-actuates various electrical switches to control the use of electrical energy. An electrical energy usage monitor, such as a kilowatt sensor 28, monitors the amount of electrical energy consumed and environmental condition monitors 30 monitors temperature, pressure, and other environmental conditions. The energy and water management computer implements a preselected energy management program to select among various electrical usage demands in accordance with electrical energy drawn, the time of day, the day of the week, and the sensed outside temperature, inside temperature gradients, and other environmental conditions.

More specifically, the energy and water management controller 20 includes a water quality subsystem 34 for monitoring the water quality computer 10 and controlling the water quality control pumps and valves 22. A chemical inventory subsystem 36 tracks the inventory of additives on hand at each remote station in conjunction with the inventory switches 24. An energy usage manager 38 implements an appropriate energy management program to operate electrical equipment and other energy usage in accordance with a preprogrammed power usage routine and environmental conditions. A pollable memory 40 stores monitored physical property levels, energy usage amounts, chemical addition and water bleed data, chemical inventories, system parameters, and the like.

A modem 42 selectively receives data from the pollable memory 40 for conveyance over communication lines, such as telephone lines, direct or dedicated lines or other data transmission lines, to the polling station B. The modem 42 further receives updated system parameters, manual override commands, control signals, program revisions, and the like from the polling station.

Figure 2A:
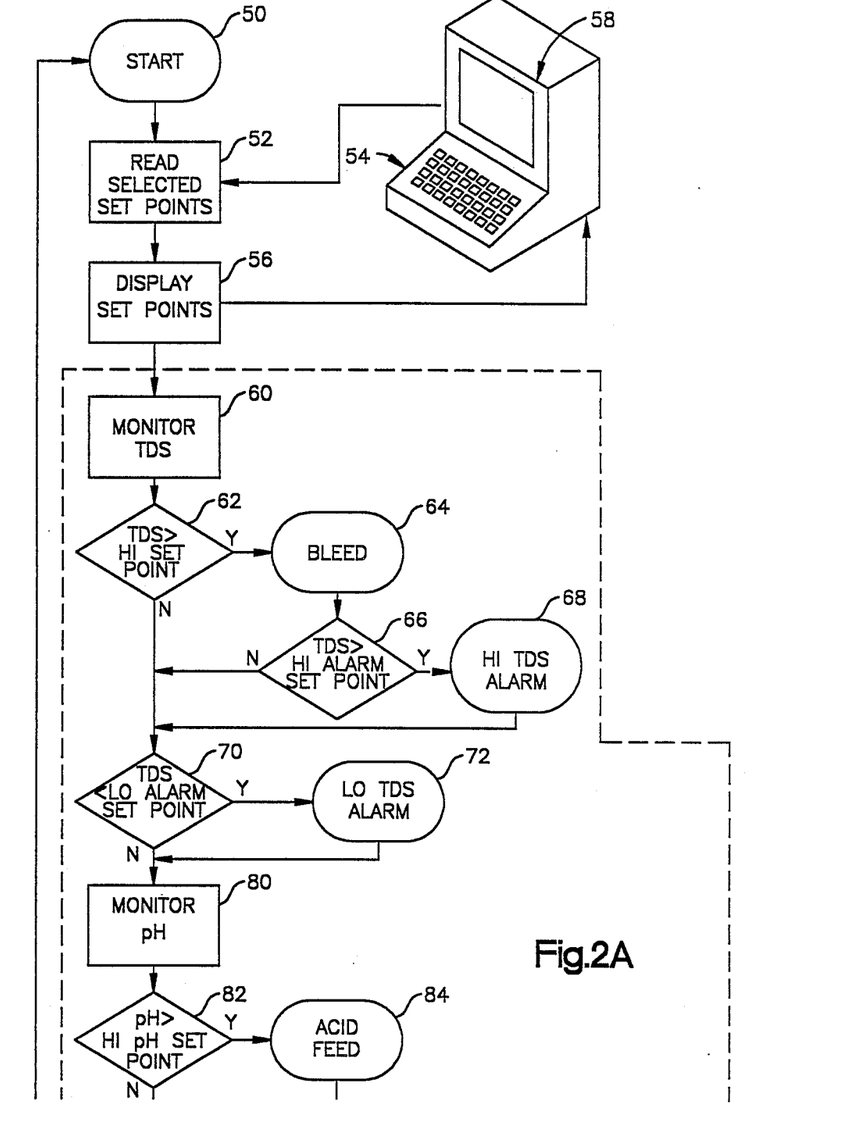
FIGS. 2A and 2B are a two-part programming flow chart for the microcomputer control of the water quality monitor of FIGS. 1A and 1B.
Figure 2B:
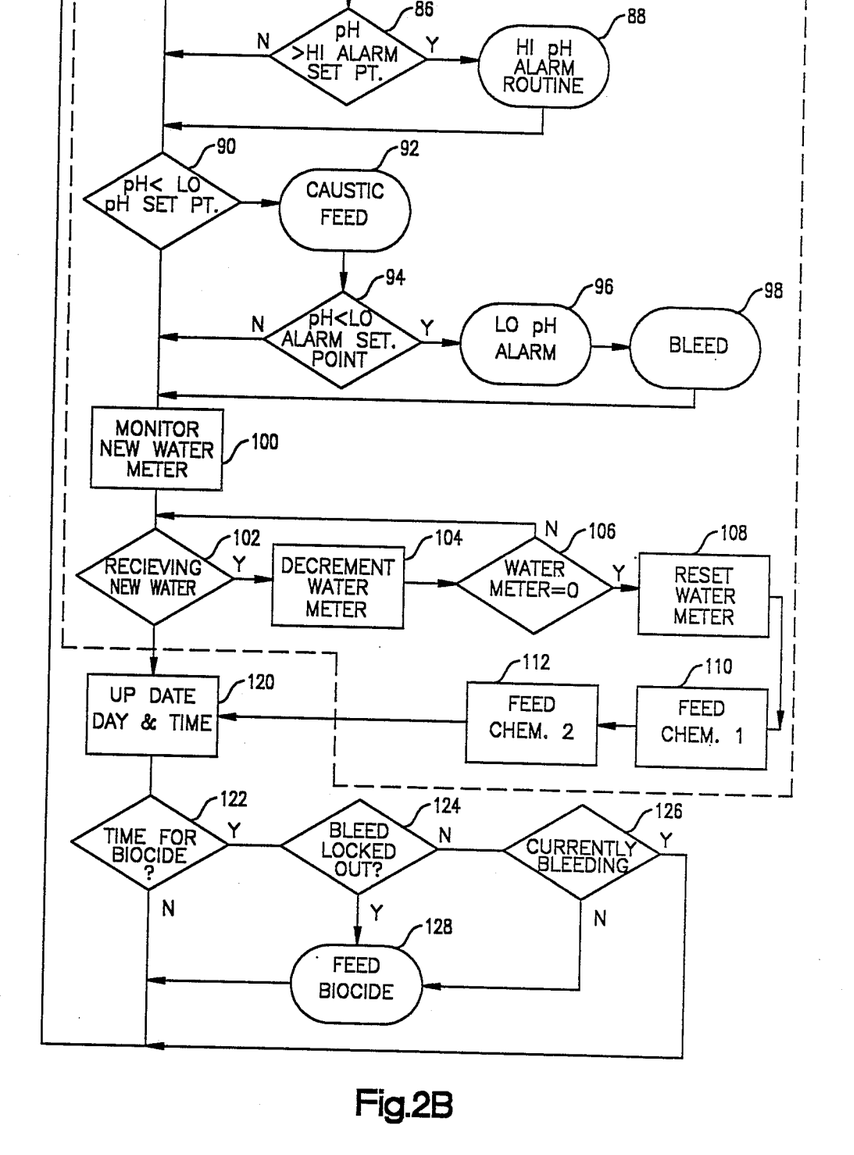

With reference to FIGS. 2A and 2B, the water quality monitor computer 10 includes a start means or step 50 for initializing the computer. A read step or means 52 reads preselected ranges or set points from memory for each monitored physical property. The set points are entered by an operator on keyboard 54 or entered remotely from one of the polling stations B. A display step or means 56 causes the selected physical property ranges or set points to be displayed on a video monitor 58.

A first physical property monitoring step or means 60 monitors a first physical property of the water, e.g. the electrical conductivity which varies as a function of the total dissolved solids. In particular, the computer program monitors the conductivity sensed by the conductivity or total dissolved solids sensor 12a. A first physical property level comparing means or step 62 compares the monitored first physical property level with a selected high set point as read at the set point read means or step 52. If the monitored conductivity shows a level of conductivity which exceeds the preselected high set point, a bleed routine 64 is initiated. The bleed routine signals the management computer 20 to open the bleed valve 22a and bleed a preselected volume of water from the water system. Thereafter, fresh water is added to replace the bled water. An alarm level comparing means or step 66 compares the monitored level of dissolved solids indicated by the monitored conductivity with a total dissolved solids alarm set point. If the total dissolved solids are higher, not only than the high set point but also higher than the high alarm set point, a high dissolved solids alarm subroutine 68 causes the alarm 16 to be activated.

A low total dissolved solids comparing means or step 70 compares the monitored total dissolved solids level with a low total dissolved solids set point. If the monitored conductivity shows that the level of total dissolved solids is below the low alarm set point, a low total dissolved solids alarm routine 72 is initiated to warn of the low total dissolved solids level.

A second physical property monitoring means or step 80 monitors the pH level as sensed by the pH sensor 12b. A second physical property or pH comparing means or step 82 compares the monitored pH level with a high pH set point as read by the set point read means or step 52. If the monitored pH level exceeds the high pH set point, an acid feed routine 84 causes the maintenance computer 20 to activate acid pump 22b to adjust the pH of the water. A high pH alarm comparing means or step 86 compares the pH with a high alarm set point which is greater than the high set point. If the pH exceeds the high alarm set point, a high pH alarm routine 88 is initiated to provide a warning of the unusually high pH level.

A low pH comparing means or step 90 compares the monitored pH level with a low pH set point. If the pH is below the low pH set point, a caustic feed means or step 92 causes a strong base, caustic or other alkalinity additive to be added to the water system. A low pH alarm comparing means or step 94 compares the monitored pH with a low alarm set point. If the pH is below the low alarm set point, a low pH alarm means or step 96 alerts the operator of the abnormally low pH condition. Further, a bleed means or step 98 calls upon the maintenance computer 20 to open bleed valve 22a and drain a preselected volume of water from the water system. In this manner, the high pH set point comparing means or step 82 and the low pH set point comparing means or step 90 function as a means for comparing the monitored pH or other physical property level with a preselected physical property range to determine whether an adjustment to the water is called for. Similarly, the acid feed means or step 84 and the caustic feed means or step 92 together function as a means or step for adjusting a chemical property of the water in response to the monitored physical property or pH level being outside of the preselected pH range. Optionally, a feed timer may limit the duration of the alkalinity additive or acid feed to preselected maximum duration.

A new water meter monitoring step or means 100 monitors the water meter 12c to see whether additional or replacement water is being added to the water system to replace the water drained during the bleed step. A new water comparing means or step 102 determines whether new water is being received. If new water is being received, a decrement means or step 104 decrements a water meter counter. A water meter decrement monitoring step or means 106 monitors whether the water meter has been decremented to zero. If the water meter has not been decremented to zero, the program returns to the new water comparing means or step 102. If the water meter has been decremented to zero, a reset means or step 108 resets the water meter. In this manner, the water meter monitoring system determines whether or not a preselected amount of replacement water has been added. A first chemical feed means or step 110 causes a preselected amount of a first water treatment chemical to be added to the water system. The amount of first chemical is selected in coordination with the preselected volume of received water. A second water treatment chemical feed means or step 112 feeds a preselected volume of a second water treatment chemical to the water feed system. Analogously, additional chemical and biocide feed means or steps may be provided.

A time and date update means or step 120 updates a time and date counter. A third or biocide comparing means or step 122 compares the data and time from the time and date means or step 120 with preselected times at which biocide chemicals are to be added. If biocide is called for, a bleed lock-out checking means or step 124 blocks the bleed valve 22a against draining fluid and checks that the bleed valve is so locked. If the bleed valves fail to lock, a bleed checking means or step 126 determines whether the bleed valve is currently open. When the bleed valve is locked out and closed, a biocide feed means or step 128 feeds a preselected dose of biocide into the feed system. Optionally, a variety of biocides may be individually fed at the same or different times. Thereafter, the program returns to the start step or means 50 and repeatedly cycles therethrough. In this manner, various physical properties of water in the water system are repeatedly monitored and appropriate corrections to the water quality are made.

Figure 3A:
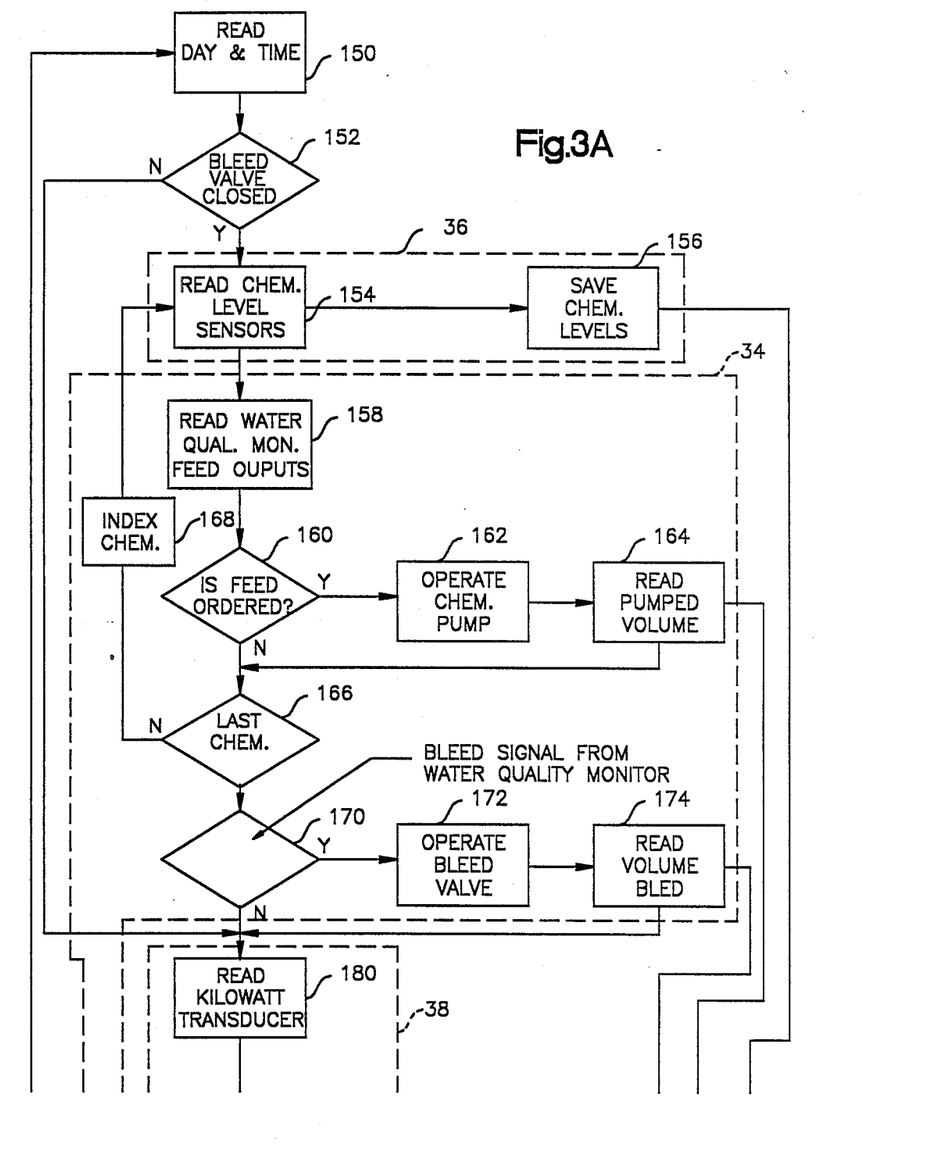
FIGS. 3A and 3B together form a programming flow chart of the energy and water management processor of FIGS. 1A and 1B; and, FIG. 4 is an operating flow chart for the polling computer of FIGS. 1A and 1B.
Figure 3B:
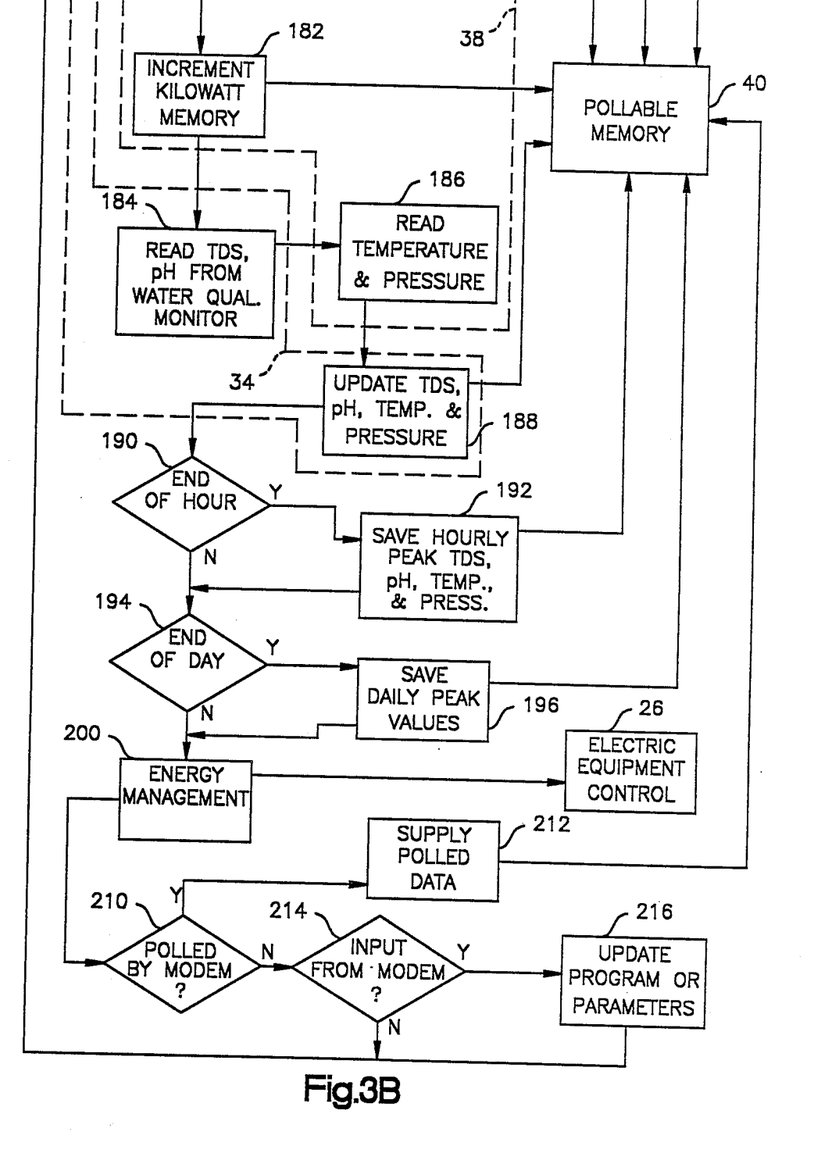

With particular reference to FIGS. 3A and 3B, the energy and water management computer 20 runs through a continuous loop. At a read step or means 150, the management computer reads the current date and time. At a bleed valve status step or means 152, the status of the bleed valve is determined. If the bleed valve is closed, i.e. the system is not bleeding, a chemical quantity on hand monitoring step or means 154 reads the chemical quantity level switches 24 to determine the quantity of each treatment chemical on hand. A memory control means or step 156 causes the pollable memory 40 to store the current quality of the water treatment chemicals.

At a read step or means 158, the management computer 20 polls the water quality monitor computer 10. A feed determined step or means 160 determines whether the feed of water treatment chemicals has been called for. If the feed of water treatment chemicals is called for, a pump control step or means 162 causes the appropriate chemical pump 22 to add a preselected volume of water treatment chemical. The volume of chemical actually pumped into the treatment water is monitored by a means or step 164 and stored in the pollable memory 40.

In the preferred embodiment, each of the available water treatment chemicals is monitored and fed individually. To this end, a comparing means or step 166 determines whether the program has cycled through all of the available water treatment chemicals. If not, a water treatment chemical index means or step 168 indexes the routine to the next chemical and repeats the monitoring and feeding operations for each chemical individually.

A bleed means or step 170 determines whether a bleed signal has been polled from the water quality computer 10. If a bleed signal is read, a bleed valve operating means or step 172 opens the bleed valve for the preselected duration. A bleed volume monitor means or step 174 determines the actual volume of water bled and causes the pollable memory 40 to store the determined volume.

An energy read step or means 180 reads the kilowatt transducer 28 or other energy usage sensors to determine energy usage. A kilowatt memory incrementing means or step 182 indexes the kilowatt memory to update the total energy consumption, which energy consumption is stored in the pollable memory 40. A physical property read step or means 184 polls the water quality computer 10 to retrieve the total dissolved solids and pH levels read thereby. A temperature and pressure read means or step 186 reads the temperature and pressure read by the environmental condition transducers 30. A memory update means or step 188 updates the pollable memory 40 with the current total dissolved solids, pH, temperature and pressure readings.

A time determining means or step 190 determines whether a first recording interval, in the preferred embodiment an hour, has passed. At the end of an hour, a memory control means or step 192 causes only the peak total dissolved solids, pH, temperature, and pressure recorded in the preceeding hour to be retained by the pollable memory 40 along with an indication of the corresponding hour. A second recording interval determining means or step 194 determines whether a longer recording interval, in the preferred embodiment a 24 hour day, has elapsed. If the longer recording interval has elapsed, a memory control means or step 196 determines the peak value read during the preceeding 24 hours and causes each peak to be stored in conjunction with an indication of the 24 hour recording period.

An energy management step or means 200 implements a conventional energy management program. The conventional energy management program turns preselected loads on and off at selected times during the day. Moreover, the timing at which the loads are turned on and off is adjusted in accordance with the monitored outside temperature and pressure. For example, the energy management means or step 200 may operate hot water heaters starting at 6:00 a.m. to bring the building's hot water supply up to temperature. Only after the hot water supply is up to temperature are the room air circulating fans actuated. Depending on the monitored outside temperature, outside air may be drawn into the building or an air conditioning or heating units may be operated. At various times during the day, air conditioning compressors may be stopped and the hot water heaters actuated to bring the hot water supply back up to temperature. Moreover, the duty cycle of various air conditioning compressors is varied to maintain the greatest cooling on the sunny side of the building with lesser or no cooling on the shady side. Near the end of the normal working day, power to the hot water heaters is terminated. Closer to the end of the working day, at a time determined from the outside temperature, the air conditioner compressors are de-activated. At a selected time, the air circulating fans are also de-activated. Optionally, other electrical and energy loads may be controlled and managed as may be appropriate.

A means or step 210 determines whether or not the information in the pollable memory 40 is being polled by one of the polling stations B. If a polling station is requesting information, a memory control means or step 212 retrieves the polled information from the pollable memory 40 and supplies it to the modem 42 to be conveyed to the polling station. A program modification means or step 214 determines whether the energy management program, the water quality program, other programs or parameters therefor are to be adjusted from the polling station. If so, a program and parameter updating means 216 implements the called for program and parameter changes.

In this manner, the management computer continuously cycles through various read and update routines. Specifically, it cyclically reads the water quality physical properties monitored by the water quality computer and monitors the water quality computer to determine when the addition of water treatment chemicals or the bleeding of water from the water system are required. The management computer causes the appropriate chemical addition or bleeding to be undertaken and records the exact amounts of chemicals actually added or water actually bled. Moreover, the management computer 20 maintains a cyclically updated indication of the quantity of each treatment chemical remaining in storage for later addition to the water treatment system.

The management computer further controls electrical and other energy usage and maintains an hourly record of such controlled energy usage.

With reference again to FIGS. 1A and 1B, the central polling station B includes a computer means 250 which retrieves information through a modem 252 from each of the remote stations and prepares appropriate reports and shipping requests. In the preferred embodiment, the computer generates daily reports of abnormal conditions and monthly summary reports. A printer 254 generates man-readable reports and invoices.

Figure 4:
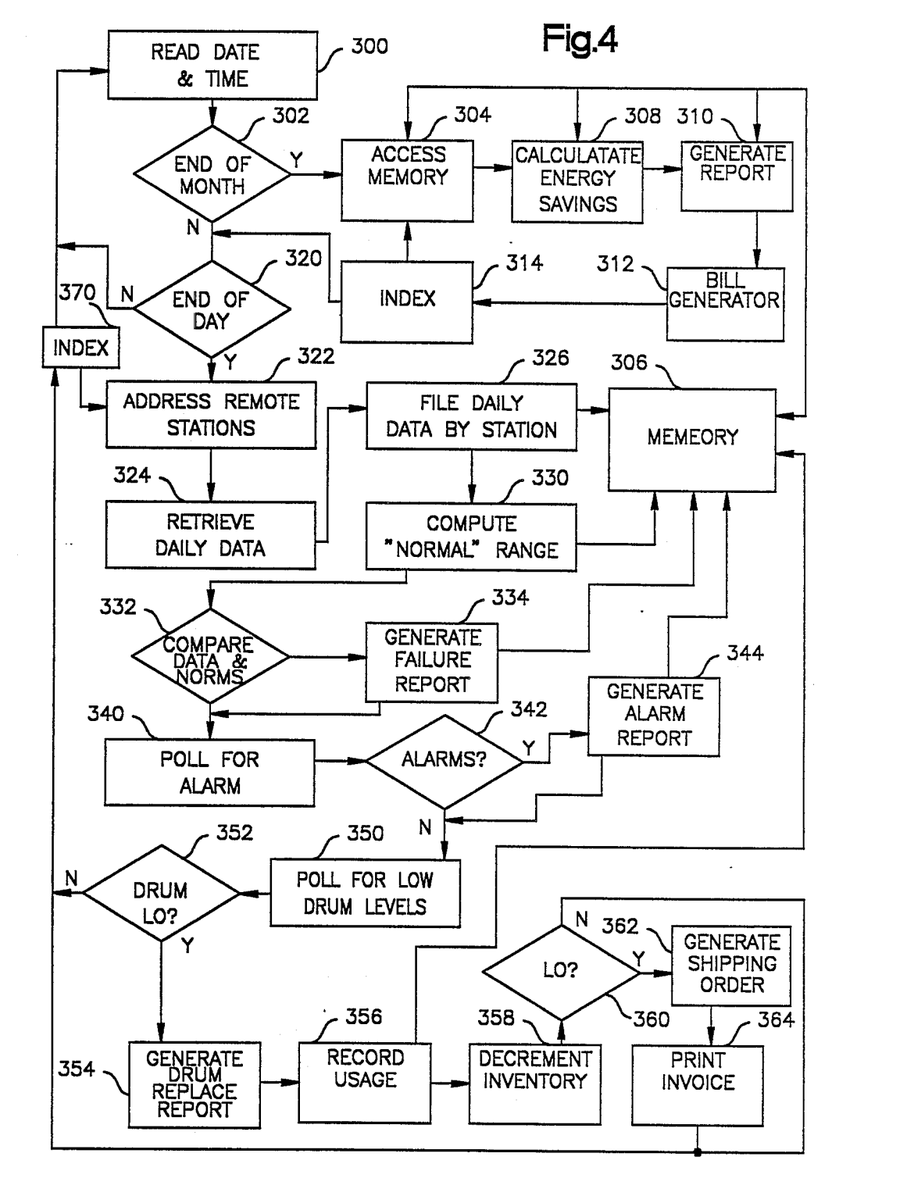

With reference to FIG. 4, the central polling computer 250 includes a read means or step 300 for reading the current date and time. An end of the month determining means or step 302 determines whether or not an end-of-the-month report is due. If an end-of-the-month report is due, a memory access means 304 accesses a main computer memory 306 to withdraw the daily and monthly data for each remote station. An energy saving means or step 308 calculates the energy savings using the present invention relative to historical data of energy consumption before the present invention was installed. A report generator 310 generates an appropriate report of energy saving and water treatment chemical consumption for the preceeding month. A bill generator 312 generates a monthly bill. In the preferred embodiment, the monthly bill includes equipment lease charges which are calculated as a percentage of energy savings. An index means or step 314 indexes the memory access means or step 304 until monthly reports and bills have been generated for each remote station.

A daily timer means or step 320 determines the end of the day or other recording period. At the end of the recording period, each of the remote stations is serially addressed by a remote station addressing means or step 322. A data retrieval means or step 324 retrieves the daily data from the pollable memory 40 of the addressed remote station. A memory control means or step 326 files the daily data from each remote station in the central polling station memory 306. This provides an ongoing record of the energy and water treatment chemical consumption.

A computing means or step 330 accesses the polling station memory 306 to retrieve prior consumption data and recomputes a normal consumption range for each monitored physical property, energy usage, or consumed chemical based on historic data. If a comparing means or step 332 determines that the received data is not within the computed normal ranges, a report generating means or step 334 generates an abnormal condition or system failure report.

An alarm polling means or step 340 polls the remote station pollable memory 40 to determine whether any alarm conditions occurred during the preceeding reporting period. If a comparing means or step 342 determines that alarms have been triggered, a report generator 344 generates an appropriate report of the alarm conditions. In this manner, reports are automatically generated reporting any abnormal conditions at each remote station. In the preferred embodiment, the daily reports are forwarded automatically to both the remote station and a centrally located engineer responsible for the remote station.

An inventory polling means or step 350 polls the remote station for low chemical inventory data. A comparing means or step 352 determines whether any chemical drums are low or have changed in volume from nearly empty to nearly full indicating that the drum has been replaced since the last polling. If a drum has been replaced, a report generator means or step 354 generates a drum replacement report. A memory control means or step 356 causes the polling computer memory 306 to record the chemical consumption. An inventory control means or step 358 decrements the number of drums in inventory at the polled station. If a drum inventory comparing means or step 360 determines that the number of drums of the chemical in inventory are below a preselected low leve, a shipping order generator 362 generates a shipping order to ship additional drums of the chemical to the polled station. An invoice step or means 364 causes an invoice for the shipped chemicals to be generated.

A remote station indexing means 370 causes the next remote station to be addressed and the data retrieval and report generation process to be repeated until each of the remote stations has been accessed. In this manner, each of the remote stations is accessed daily to determine water quality data, water treatment chemical consumption, energy consumption, and the like. Responsive to the daily information, daily reports of abnormal conditions and shipping orders for replacement chemicals are generated. Each month a summary report is generated.

Referring again to FIGS. 1A and 1B, the remote stations may be polled from most any telephone. With a portable modem 400 and an acoustic coupler 402, minicomputer terminal, or other portable access device, an engineer can selectively address a selected remote station to monitor its operation or correct a malfunction.

The invention has been described with referenced to the preferred embodiment. Obviously, modifications and alterations will occur to others upon reading and understanding the preceeding detailed description of the preferred embodiment. It is intended that the invention be construed as including all such modifications and alterations in so far as they come within the scope of the appended claims or the equivalents thereof.

Having thus described a preferred embodiment of the invention, the invention is now claimed to be:

1. A method of telemetrically monitoring water treatment and an inventory of water treatment chemicals and adjusting water properties in a recirculating system including a boiler, cooling tower or scrubber with a computer-based system, comprising:
- at each of a plurality of remote locations, automatically monitoring by telecommunications the level of a plurality of physical properties of water in said recirculating system including conductivity and temperature, at least one of the physical properties being indicative of dissolved solids;
- automatically monitoring the inventory of water treatment chemicals;
- establishing a range of temperature and conductivity of the water at which said temperature and conductivity is to be maintained;
- periodically automatically comparing the monitored levels of inventory, temperature, and conductivity with the established ranges for each with the computer-based system;
- automatically changing the conductivity measurement of the water as required to keep the conductivity in the established range by either addition of a first water treatment chemical from said inventory or bleeding water from the system and adding fresh water;

periodically automatically monitoring the levels of inventory of the chemicals remaining; and automatically telemetrically monitoring the amount of new water added to the system.

2. The method as set forth in claim 1 further including at each remote location, the steps of:

automatically monitoring the level of pH of the water;

establishing a range of pH for the water; and automatically comparing the level of pH with the range and automatically bringing the pH to within the range if the pH level is outside of the range by the addition of an acid or caustic chemical.

3. The method as set forth in claim 2 further including adding said first water treatment chemical to the water when new water is added.

4. The method as set forth in claim 3 further including at each remote location, the step of automatically monitoring a quantity of the first water treatment chemical on hand and periodically storing the first chemical quantity and, in a periodic polling step, automatically polling the stored first chemical quantity.

5. The method as set forth in claim 4 further including the step of comparing the polled first chemical quantity with a preselected quantity specification and automatically invoicing a shipment of additional first chemical in response to the polled first chemical quantity being below the preselected quantity specification.

6. The method as set forth in claim 3 further including:

at each remote location, monitoring a second physical property indicative of water quality;

comparing the monitored second physical property with a second preselected physical property range;

in response to the monitored second physical property being outside of the second range, changing a concentration of at least a second chemical in the water;

monitoring a quantity of the second chemical at the remote location;

storing an indication of the monitored second chemical quantity;

at a polling location, periodically polling the stored second chemical quantity indications stores at each of the remote locations;

comparing the polled second chemical quantity indications at each of the remote locations with a preselected second chemical quantity specification;

in response to the polled second chemical quantity indication being outside of the second chemical quantity specification, automatically invoicing a shipment of the second chemical to each remote location which is outside of the second chemical quantity specification.

7. The method as set forth in claim 3 wherein the step of monitoring the first chemical quantity includes monitoring a level of the first chemical within a container and monitoring the number of containers.

8. The method as set forth in claim 3 further including:

at each remote location, the step of monitoring an indication of an amount of the first chemical which is added and storing the monitored, added first chemical amount; and, at a polling location, the step of periodically polling the stored first chemical added amount at each of the plurality of remote locations, comparing each polled first chemical added amount with a preselected first chemical added range, and in response to the polled first chemical added amount being outside the first chemical added range, providing a man-readable indication thereof, whereby over and under addition of treatment chemicals is monitored from the polling location.

9. The method as set forth in claim 8 further including at the polling location, the steps of generating a written report indicating at least the quantity of the first chemical at each remote location and added amounts of the first chemical which are outside of the first chemical added range.

10. The method as set forth in claim 2 further including:

at each remote location, the steps of monitoring energy usage and storing an indication of the amount of energy used; and, from a polling location, the step of periodically polling the stored energy usage indication and generating a report of energy usage.

11. The method as set forth in claim 10 further including at the polling location, the step of comparing the polled energy usage with a stored, historical energy usage and wherein the report generating step further includes generating a report of energy savings.

12. The method as set forth in claim 1 further including at each remote location, the steps of:

monitoring the adjustment of the monitored physical property of the water;

storing an indication of the manner in which the water physical property was adjusted; and, polling the stored indications of the manner in which the water physical property was adjusted.

13. The method as set forth in claim 12 wherein the step of adjusting the water physical property includes adding said first water treatment chemical to the water and wherein the step of monitoring the physical property adjustment at each remote location includes monitoring a first duration during which the first water treatment chemical added to the water.

14. The method as set forth in claim 13 further including the step of generating a man-readable report indicative of at least first water treatment chemical and energy usage at each remote location.

15. The method as set forth in claim 14 further including the step of comparing each polled first chemical addition duration with preselected duration tolerances and providing an indication at least when the first chemical addition duration is outside the preselected duration tolerances, whereby chemical treatment apparatus malfunctions are noted.

16. A computer-based apparatus for telemetrically monitoring water treatment and an inventory of water treatment chemicals and adjusting water properties in a recirculating system including a boiler, cooling tower or scrubber the apparatus comprising;

a remote water property monitoring means for telemetrically monitoring at least a plurality of physical properties of water in the recirculating system including conductivity and temperature at a remote location, the conductivity being indicative of dissolved solids;

means for establishing a range of temperature and conductivity of the water at which said temperature and conductivity is to be maintained;

automatic comparing means for comparing the temperature and conductivity level with the preselected range of temperature and conductivity;

automatic means for bleeding water from the recirculating system and automatic means for adding fresh water to the system being operatively connected to the automatic comparing means, for bleeding water and adding fresh water in response to one of the monitored physical property levels being outside of a preselected physical property range;

an automatic chemical adding means for adding at least a first chemical to the water, the chemical adding means being operatively connected with the automatic comparing means for adding the water treatment chemical to the water in response to one of the monitored physical property levels being outside of the preselected physical property range;

an automatic chemical quantity monitoring means for monitoring a quantity of the water treatment chemicals at the remote location;

a storage means for storing the monitored chemical quantity;

a polling computer means for periodically polling the stored chemical quantity in each of a plurality of storage means and comparing each polled chemical quantity with a chemical quantity specification.

17. The apparatus as set forth in claim 16 further including an energy monitoring means for monitoring energy usage, a computer means for storing an indication of energy used and preselected range of energy and an energy comparing means for comparing the energy used and the preselected range of energy.

* * * * *